(12) United States Patent
Bengtsson et al.

(10) Patent No.: US 10,485,927 B2
(45) Date of Patent: Nov. 26, 2019

(54) METHOD FOR ASSEMBLING A DRUG DELIVERY DEVICE AND DRUG DELIVERY DEVICE FORMED BY THE METHOD

(71) Applicant: Novo Nordisk A/S, Bagsvaerd (DK)

(72) Inventors: Henrik Bengtsson, Taastrup (DK); Ronan Carroll, Tisvildeleje (DK); Emil Gram Spork, Copenhagen N (DK)

(73) Assignee: Novo Nordisk A/S, Bagsvaerd (DE)

( * ) Notice: Subject to any disclaimer, the term of this patent is extended or adjusted under 35 U.S.C. 154(b) by 97 days.

(21) Appl. No.: 15/735,784

(22) PCT Filed: Jul. 1, 2016

(86) PCT No.: PCT/EP2016/065621
§ 371 (c)(1),
(2) Date: Dec. 12, 2017

(87) PCT Pub. No.: WO2017/001694
PCT Pub. Date: Jan. 5, 2017

(65) Prior Publication Data
US 2018/0140776 A1    May 24, 2018

(30) Foreign Application Priority Data
Jul. 1, 2015  (EP) .................................. 15174921

(51) Int. Cl.
*A61M 5/24*   (2006.01)
*A61M 5/31*   (2006.01)
*A61M 5/315*  (2006.01)

(52) U.S. Cl.
CPC ............ *A61M 5/24* (2013.01); *A61M 5/3146* (2013.01); *A61M 5/31515* (2013.01);
(Continued)

(58) Field of Classification Search
CPC .. A61M 5/24; A61M 5/31551; A61M 5/2033; A61M 5/20; A61M 5/31553;
(Continued)

(56) References Cited

U.S. PATENT DOCUMENTS 6,241,709 B1   6/2001  Bechtold et al.
8,585,658 B2  11/2013  Forstreuter
(Continued)

FOREIGN PATENT DOCUMENTS

EP     1541185    6/2005
WO    97/10864    3/1997
(Continued)

*Primary Examiner* — Manuel A Mendez
(74) *Attorney, Agent, or Firm* — Wesley Nicolas

(57) ABSTRACT

The present invention relates to a method of assembling a drug delivery device which in the assembled state defines a distal housing component (102) that houses a piston equipped cartridge (189), and a proximal housing component (101) that houses a dose setting and expelling mechanism. The method includes the steps of arranging the cartridge (189) in the distal housing component (102), arranging a nut element (140) threadedly engaged with a piston rod (107) in the distal housing component (102), and securing the nut element (140) relative to the distal housing component (102) into a selective one of a series of predetermined relative orientations for obtaining a predetermined axial clearance or abutment between the piston rod (107) and the piston of the cartridge (189). The invention further relates to a drug delivery device assembled according to the method.

15 Claims, 4 Drawing Sheets

(52) U.S. Cl.
CPC .... *A61M 5/31573* (2013.01); *A61M 5/31581* (2013.01); *A61M 2005/2407* (2013.01)

(58) Field of Classification Search
CPC .......... A61M 5/31585; A61M 5/31541; A61M 5/2448; A61M 5/3158; A61M 5/3202; A61M 5/31568; A61M 5/31535; A61M 5/31511; A61M 5/19; A61M 5/31543; A61M 5/3157; A61M 5/31536; A61M 5/5086; A61M 5/3155; A61M 5/31583; A61M 5/31501; A61M 5/31525; A61M 5/31528; A61M 5/315; A61M 5/31515; A61M 5/31596; A61M 5/31513; A61M 5/3204; A61M 5/14566; A61M 5/31573; A61M 5/31581
See application file for complete search history.

(56) References Cited

U.S. PATENT DOCUMENTS

| | | |
|---|---|---|
| 9,707,352 B2 | 7/2017 | Helmer et al. |
| 9,867,945 B2 | 1/2018 | Nzike et al. |
| 10,201,662 B2 | 2/2019 | Morris et al. |
| 2012/0283662 A1 | 11/2012 | MacDonald et al. |

FOREIGN PATENT DOCUMENTS

| | | |
|---|---|---|
| WO | 9938554 A1 | 8/1999 |
| WO | 200119434 A1 | 3/2001 |
| WO | 2002/092153 A2 | 11/2002 |
| WO | 2006/128794 A2 | 12/2006 |
| WO | 2007017051 A1 | 2/2007 |
| WO | 2009095332 A1 | 8/2009 |
| WO | 2009/132777 A1 | 11/2009 |
| WO | 2010/139634 A1 | 12/2010 |
| WO | 2010149209 A1 | 12/2010 |
| WO | 2011/039229 A1 | 4/2011 |
| WO | 2011089246 A1 | 7/2011 |
| WO | 2011113868 A1 | 9/2011 |
| WO | 2012/037938 A1 | 3/2012 |
| WO | 2012/049144 A1 | 4/2012 |
| WO | 2013156224 A1 | 10/2013 |
| WO | 2014/029681 A2 | 2/2014 |
| WO | 2014/029683 A1 | 2/2014 |
| WO | 2014/029724 A1 | 2/2014 |
| WO | 2014060369 A1 | 4/2014 |
| WO | 2014/139918 A1 | 9/2014 |
| WO | 2014/139920 A1 | 9/2014 |

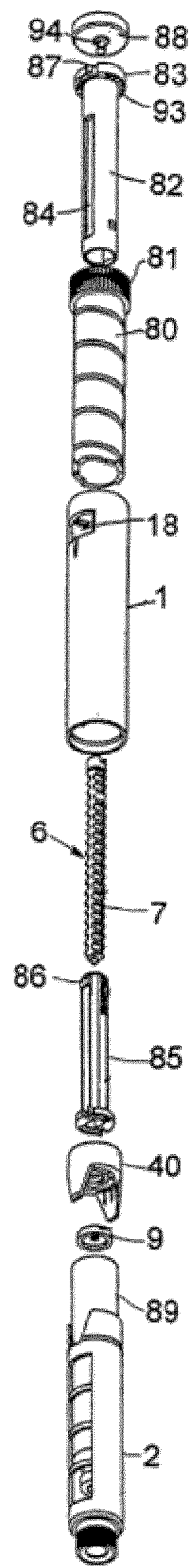
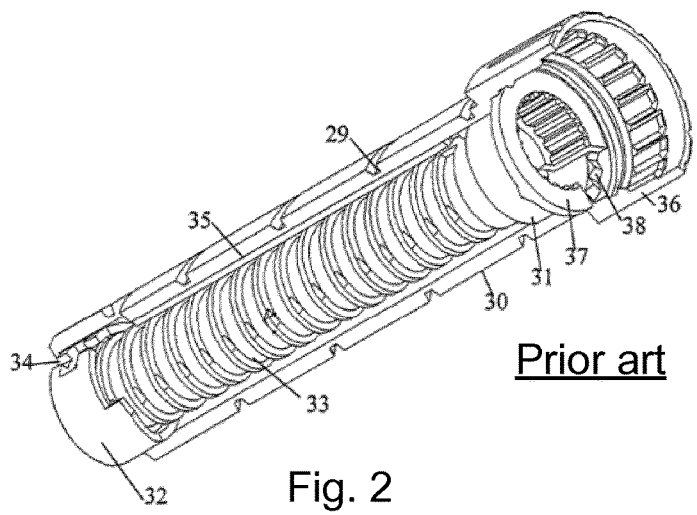
Prior art
Fig. 2
Prior art
Fig. 1

METHOD FOR ASSEMBLING A DRUG DELIVERY DEVICE AND DRUG DELIVERY DEVICE FORMED BY THE METHOD

CROSS-REFERENCE TO RELATED APPLICATIONS

This application is a 35 U.S.C. § 371 National Stage application of International Application PCT/EP2016/065621 (published as WO 2017/001694), filed Jul. 1, 2016, which claims priority to European Patent Application 15174921.5, filed Jul. 1, 2015, the contents thereof which are incorporated by reference in their entirety.

The present invention relates to an assembly of components for a drug delivery device that allows a user to select single or multiple doses of an injectable liquid drug and to dispense the set dose of the product and to apply said product to a patient, preferably by injection. In particular, the present invention relates to a method of assembling such drug delivery devices.

BACKGROUND

In the disclosure of the present invention reference is mostly made to drug delivery devices used e.g. in the treatment of diabetes by delivery of insulin, however, this is only an exemplary use of the present invention.

Drug delivery devices allowing for multiple dosing of a required dosage of a liquid medicinal product, such as liquid drugs, and further providing administration of the liquid to a patient, are as such well-known in the art. Generally, such devices have substantially the same purpose as that of an ordinary syringe. Drug delivery devices of this kind have to meet a number of user specific requirements. For instance in case of those with diabetes, many users will be physically infirm and may also have impaired vision. Therefore, these devices need to be robust in construction, yet easy to use, both in terms of the manipulation of the parts and understanding by a user of its operation. Further, the dose setting must be easy and unambiguous and where the device is to be disposable rather than reusable, the device should be inexpensive to manufacture and easy to dispose. In order to meet these requirements, the number of parts and steps required to assemble the device and an overall number of material types the device is made from have to be kept to a minimum.

Typically, the liquid drug to be administered is provided in a cartridge that has a moveable piston or bung mechanically interacting with a piston rod of an expelling mechanism of the drug delivery device. By applying thrust to the piston in distal direction, a predefined amount of the liquid drug is expelled from the cartridge. Due to inevitable manufacturing tolerances there may for instance persist axial clearance between a cartridge's piston and the piston rod. Typically, prior to a primary use of the device, an end-user has to conduct a so-called priming of the expelling mechanism in order to ensure, that already with an initial dose setting and a first subsequent dose dispensing step, an accurate amount of the liquid drug is dispensed in a predefined way. An initial dose setting and expelling of a minor dose may in certain situations also be required for removing any air present in the cartridge and/or a connected needle and for performing a flow check.

Document WO 99/38554 A1 discloses several embodiments of injection devices each suitable for forming a disposable device wherein a liquid drug cartridge is inserted into the device during assembly in a production line.

State of the art pen-type drug delivery devices that incorporate a dose setting feature often include a so-called end-of-content limiter to prevent a user from selecting a size of a dose which exceeds the amount of liquid drug remaining in a cartridge of the device. References WO 01/19434 A1, WO 2006/128794 A2, WO 2010/149209 A1 and WO 2013/156224 A1 include disclosure of such end-of-content limiters.

In the production line, during final assembly operations of the devices, at least a part of the priming is typically carried out using the dose setting and expelling mechanism so that users will experience virtually consistent requirement for a priming operation across individual pen samples irrespective of the initial gap between the piston rod and the piston which emanates from tolerance variations. Reference WO 2009/095332 A1 discloses devices wherein a distance between the distal end of a piston rod means and the plunger is minimized or reduced to zero. WO 2011/113868 A1 provides a further disclosure of related methods and devices.

SUMMARY

It is an object of the present invention to provide a drug delivery device featuring improved and facilitated clearance reduction or clearance elimination. It is a further object of the invention to provide a simplified and robust method of eliminating clearance in a drug delivery device. Finally, it is an object of the invention to provide manufacture of drug delivery devices providing consistently uniform and predictable total doseable amount of liquid drug from a held cartridge.

In the disclosure of the present invention, embodiments and aspects will be described which will address one or more of the above objects or which will address objects apparent from the below disclosure as well as from the description of exemplary embodiments.

In a first aspect, the present invention relates to a method of assembling a drug delivery device defining a distal drug outlet end and an opposite proximal end, which in the assembled state defines a distal housing component secured to a proximal housing component, wherein:

the distal housing component holds a cartridge comprising a liquid drug and a piston slideable arranged therein in an axial direction, a nut element having a threaded opening and a piston rod comprising an outer thread engaged with the threaded opening of the nut element, and the proximal housing component houses a dose setting and expelling mechanism comprising a driver adapted to rotationally couple to the piston rod so as to prevent relative rotational movement but allow relative axial slideable engagement between the driver and the piston rod, the driver being rotatable during a dose expelling procedure to induce rotation on the piston rod to rotate the piston rod through the nut element and causing a dose of drug to be expelled.

The method of assembling the drug delivery device comprises the steps of:

a1) providing the distal housing component and arranging the cartridge in the distal housing component, a2) providing the piston rod and the nut element in threaded engagement with each other to form a piston rod assembly, a3) arranging the piston rod assembly relative to the distal housing component so that the piston rod is arranged with an initial axial clearance relative to the piston of the cartridge, a4) rearranging the nut element and the distal housing component relative to each other in one of a series of predetermined (variable) relative orientations to reduce said initial axial clearance while rotationally maintaining the piston rod in a predetermined rotational orientation relative to the distal housing component to obtain a predetermined axial clearance or abutment between the piston rod and the piston, a5) securing the nut element relative to the distal housing component into one of said series of predetermined relative orientations for maintaining said predetermined axial clearance or abutment between the piston rod and the piston, b1) providing the proximal housing component with the drive mechanism wherein the driver assumes a predetermined rotational orientation relative to the proximal housing component, c1) arranging the distal housing component and the proximal housing component relative to each other in a predetermined rotational orientation, c2) moving the distal housing component and the proximal housing component axially relative to each other so that the driver engages in axially slideable engagement with the piston rod, and c3) fixedly securing the distal housing component and the proximal housing component relative to each other in a predetermined relative axial position.

In some embodiments, in steps a1) and a2), the steps of providing the distal housing component and providing the nut element comprise configuring the distal housing component and the nut element so that the nut element and the distal housing component, in an initial state, are positionable relative to each other in a series of predetermined variable positions for varying the axial position of the piston rod relative to the piston of the cartridge and wherein the nut element is selectively fixable relative to the distal housing component in each of said predetermined variable positions.

In some embodiments, in step c2), the piston rod is held rotationally stationary relative to the distal housing component and the driver is held rotationally stationary relative to the proximal housing component.

In step a3) of arranging the piston rod assembly relative to the distal housing component the nut element is brought into engagement with the distal housing component where said engagement allows at least one degree of freedom for relative movement to be performed.

In some embodiments, in the course of step a4), engagement between the nut element and the distal housing component is maintained.

In some embodiments, in step a5) of securing of the nut element relative to the distal housing component, the nut element becomes permanently secured in a final position relative to the distal housing. In some embodiments, said permanently securing occurs prior to step c3) of fixedly securing the distal housing component and the proximal housing component relative to each other. In other embodiments, the nut element is releasably locked relative to the distal housing component.

In some embodiments, permanent attachment between the nut element and the distal housing component may be performed using any suitable fastening method such as by means of an adhesive or joining using laser radiation, ultrasonic welding or induction welding. Still alternative methods include use of mechanical fastening elements.

In some embodiments the drug delivery device forms a disposable device wherein the cartridge mounted within the device cannot be replaced with a new cartridge. In some embodiments, in step c3) the distal housing component and the proximal housing component are permanently secured relative to each other.

In one embodiment the nut element and the distal housing component are configured for in an initial state being engaged with each other in a predetermined relative axial position while allowing relative rotational position variation. During step a4) of rearranging the nut element relative to the distal housing component in one of a series of predetermined relative variable orientations, the rearranging is performed by varying the relative rotational position between the nut element and the distal housing component through a series of predetermined relative rotational positions while maintaining a fixed relative axial position between the nut element and the distal housing component.

In particular embodiments, a rotational detent mechanism may be provided between the nut element and the distal housing component enabling, during step a4), the relative rotational position between the nut element and the distal housing component to be selectably retained in one of a series of discrete predefined rotational positions.

In such embodiments the proximal housing component may be configured for cooperating with at least one of the distal housing component and the nut element for preventing relative rotation away from a selected discrete rotational position. In step a5) of securing the nut element relative to the distal housing component this is obtained during step c2) in the course of moving the distal housing component and the proximal housing component axially relative to each other.

In a further embodiment the nut element and the distal housing component are configured for in the initial state being engaged with each other in a predetermined relative rotational orientation while allowing relative axial position variation. During step a4) wherein rearranging the nut element relative to the distal housing component into one of a series of predetermined relative orientations, the rearranging is performed by varying the relative axial position between the nut element and the distal housing component.

The outer thread of the piston rod and the threaded opening of the nut element may define a first threaded engagement having a first lead. In some embodiments the nut element is coupled with the distal housing component via a second threaded engagement of second lead being different than the first lead of the first threaded engagement. In step a4) of rearranging the nut element relative to the distal housing component in one of a series of predetermined relative variable orientations, the rearranging is performed by operating the nut element through its threaded engagement with the distal housing component thereby varying the relative axial position between the nut element and the distal housing component.

The dose setting and expelling mechanism may comprise a dose setting element that rotates relative to the driver during setting of a dose and wherein the dose setting element does not rotate relative to the driver during expelling of a set dose. In such configuration, the dose setting and expelling mechanism may be configured that the driver rotates with the dose setting element during expelling of a set dose.

In a second aspect of the invention an end-of-content limiter may be arranged between the driver and the dose setting element, the end-of-content limiter being configured to prevent setting of a dose which exceeds a doseable amount of liquid drug remaining in the cartridge. In this way, the expelling of incomplete doses can be prevented.

In exemplary embodiments the end-of-content limiter is engaging the driver and the dose setting element. The end-of-content limiter moves towards an end-of-content stop geometry for example provided by one of the driver and the dose setting element as the dose setting element is rotated relative to the driver for dialing up a dose.

According to any of the assembly methods described herein, in the method step a4) a predetermined axial clearance between the piston rod and the piston is obtained.

Subsequent to step c2) of providing axially slideable engagement between the driver and the piston rod, the dose setting element may be operated for rotating the driver in a predetermined angular movement to cause the piston rod to abut the piston of the cartridge.

In exemplary embodiments of drug delivery devices assembled by the described methods the drug delivery device comprises a piston washer arranged between the piston and the piston rod and adapted to transfer an axial force from the piston rod to the piston. In step a1) the piston washer may be provided and positioned adjacent the piston.

In a third aspect, the present invention relates to a drug delivery device assembled in accordance with any of the methods described herein.

In a fourth aspect, the present invention relates to a drug delivery device defining a distal drug outlet end and an opposite proximal end, wherein the drug delivery device comprises a distal subassembly and a proximal subassembly attached to the distal subassembly, wherein:
  the distal subassembly comprises a distal housing component that holds a cartridge comprising a liquid drug and a piston slideable arranged therein in an axial direction, a nut element having a threaded opening and a piston rod comprising an outer thread engaged with the threaded opening of the nut element, and
  the proximal subassembly comprises a proximal housing component that houses a dose setting and expelling mechanism comprising a driver adapted to rotationally couple to the piston rod of the distal subassembly so as to prevent relative rotational movement but allow relative axial slideable engagement between the driver and the piston rod, the driver being configured for being rotated during a dose expelling procedure to induce rotation on the piston rod to rotate the piston rod through the nut element and causing a dose of drug to be expelled.

The distal housing component and the nut element are so configured that before attaching the distal subassembly to the proximal subassembly, the nut element and the distal housing component are positionable relative to each other in a series of predetermined variable positions for varying the axial position of the piston rod relative to the piston of the cartridge and wherein the nut element is selectively fixable relative to the distal housing component in each of said predetermined variable positions.

In one embodiment, the nut element is adjustably positionable in the axial direction relative to the distal housing component by means of an axial track and groove connection. By adjusting the axial position of the nut element relative to the distal housing component the axial position of the piston rod relative to the piston of a held cartridge may be adjusted.

In a further embodiment, the nut element is fixed axially but adjustably positionable by rotation relative to the distal housing component. By adjusting the nut element in a rotational movement relative to the distal housing component the axial position of the piston rod relative to the piston of a held cartridge may be adjusted.

In a still further embodiment, the nut element is adjustably positionable in the axial direction relative to the distal housing component by means of a threaded connection between the nut element and the distal housing component. By adjusting rotational position of the nut element relative to the distal housing component the axial position of the nut element is changed. In some embodiments the outer thread of the piston rod and the threaded opening of the nut element define a first threaded engagement having a first lead. The threaded connection between the nut element and the distal housing component define a second threaded engagement of second lead being different than the first lead of the first threaded engagement. Hence, by adjusting the nut element relative to the distal housing component in a rotational movement, the axial position of the piston rod relative to the piston of a held cartridge may be adjusted.

In particular embodiments according to the fourth aspect, the drug delivery device is defined by features that are obtained by any of the foregoing embodiments of the methods discussed above.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof. In the description of exemplary embodiments reference will be made to the use of insulin.

BRIEF DESCRIPTION OF DRAWINGS

In the following the invention will be further described with reference to the drawings, wherein FIG. 1 shows a prior art injection device in an exploded view showing the various components, FIG. 2 shows schematically a prior art end-of-content limiter suitable for incorporation in an injection device similar to the one shown in FIG. 1, FIG. 3 show an exploded perspective view of components of a distal subassembly for a first embodiment according to the invention, FIGS. 4a-4f schematically show different assembly steps in assembling a device of the first embodiment, FIG. 5 show a cross sectional view of a final distal subassembly for a device of first embodiment in the state shown in FIG. 4d.

Generally, in the figures, like structures are mainly identified by like reference numerals, e.g. so that parts carrying reference no. "7" in FIG. 1 correspond to reference no. "107" in FIGS. 3 through 7, and correspond to reference no. "207" in FIGS. 8-10.

DESCRIPTION

Figure 3:
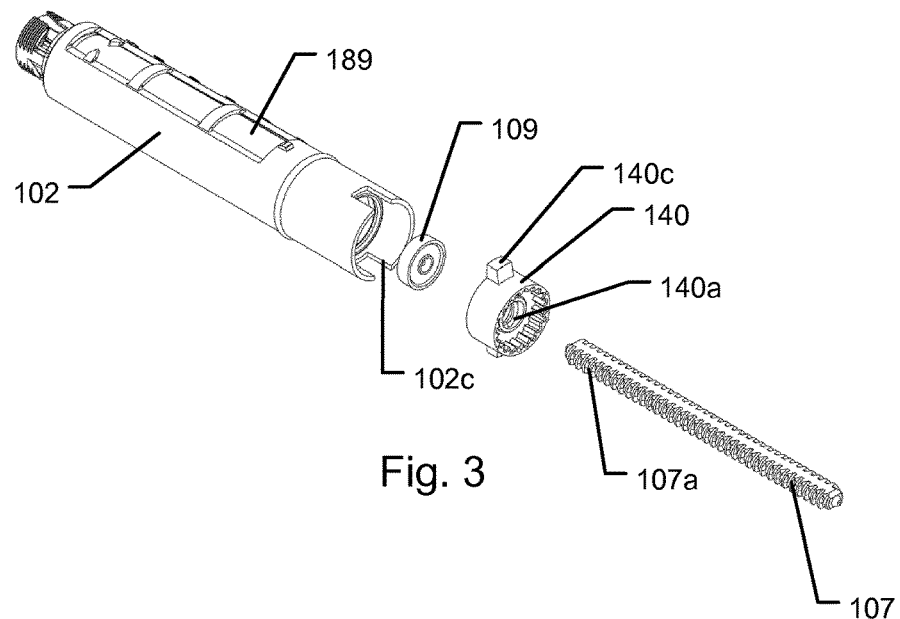

The shown figures are schematic representations for which reason the configuration of the different structures as well as their relative dimensions are intended to serve illustrative purposes only. In the following, when the term member or element is used for a given component, it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessarily can be assembled to provide a unitary or functional assembly during a given assembly procedure but is merely used to describe components grouped together as being functionally more closely related.

Shown in FIG. 1 is an exploded view of components of a prior art pen-formed drug delivery device as disclosed in connection with FIG. 15-17 of reference WO 99/38554 A1. FIG. 1 of the present disclosure is a reproduction of FIG. 17 of that reference. In the present context the device represents a "generic" prior art drug delivery device providing an example of an injection pen, e.g. a pen shaped injection device which may define a central longitudinal axis along which a piston of a held cartridge is arranged for slideable movement. The injection device is provided with a dose setting and expelling mechanism for setting and expelling one or more doses of a drug, e.g. operable for selecting the size of a dose in a dose setting procedure and expelling the set dose during a dose expelling procedure. A drug delivery device closely related to the device shown in FIG. 1 is marketed by Novo Nordisk as NovoPen FlexPen®.

More specifically, the pen device shown in FIG. 1 comprises a cap part (not shown) and a main part having a proximal body or drive assembly portion with a proximal housing component 1 in which a drug expelling mechanism is arranged or integrated, and a distal housing component 2 forming a cartridge holder portion in which a drug-filled transparent cartridge 89 (with a non-referenced distal needle-penetrable septum) can be arranged and retained in place. The distal end of the distal housing component 2 thus forms a drug outlet.

Only components directly necessary for the understanding of the present disclosure will be described herein. For the full description of the expelling mechanism reference is made to WO 99/38554 A1 which is hereby incorporated by reference.

In the fully assembled state, the distal housing component 2 is fixedly attached to the proximal housing component 1, e.g. by an axial snap connection, the distal housing component 2 having openings allowing a portion of the cartridge 89 to be inspected. The cartridge may for example contain an insulin, GLP-1 or growth hormone formulation. The device is designed to irreplaceably accommodate a cartridge 89 inserted through a proximal receiving opening in the distal housing component 2, the cartridge being provided with a piston driveable by a piston rod forming part of the expelling mechanism. A piston washer 9 may be located between the piston rod and the piston for transferring axial forces exerted by the piston rod to the piston.

Again referring to FIG. 1, a nut element 40 is fixedly secured to the distal housing component 2 at a predefined axial location thereof. The nut element 40 defines a central opening extending a along a central axis of the injection device, the opening defining an inner thread. A piston rod 7 includes an outer thread adapted to engage the inner thread of the nut element 40. The piston rod 7 further includes a longitudinal recessed track 6, a pair of flattened surfaces or similar longitudinal extending geometry for cooperating with a mating geometry of a driver tube 85 of the expelling mechanism to enable relative axial movement between the piston rod 7 and the driver tube 85 but prevent relative rotation. In the shown embodiment, the driver tube 85 is part of a multi-piece driver comprising driver tube 85 and bushing 82. Driver tube 85 and bushing 82 are configured for rotating together but to be axially displaceable relative to each other. Driver tube 85 is mounted for rotation at an axially fixed location with respect to proximal housing component 1. Driver tube 85 is rotated during dose expelling but remains non-rotatable during dose setting. A dose setting element formed as a scale drum 80 is mounted in a thread of the proximal housing component 1 and arranged to encircle and axially overlap bushing 82. During dose setting the scale drum 80 is dialed up by rotating in the thread of proximal housing component 1. Scale drum 80 is thus moved in a proximal direction relative to the proximal housing component 1 to extend proximally a distance proportional to the size of the set dose. During this dose setting procedure, the bushing 82 is moved along axially but bushing is prevented from rotating relative to the housing. A set dose is expelled by a user forcing an injection button 88 in the distal direction. During this, the scale drum 80 is rotated back towards an initial position. The bushing 82 is coupled to the scale drum 80 so that it rotates with the scale drum 80 during injection. The driver tube 85 is forced to rotate as well and acts to rotate the piston rod 7 through the nut element 40. In accordance herewith the piston rod 7 transfers a force in the distal direction forcing the piston of the cartridge 89 to move distally for expelling a quantity equal to size of the set dose.

Particular variants of the injection pen shown in FIG. 1 may include a dose setting limiter which prevents setting of a dose exceeding the doseable amount of liquid drug remaining in the cartridge of the injection device. One suitable dose setting limiter, i.e. a so-called "end-of-content limiter" is disclosed and shown in FIG. 3 of WO 01/19434 A1, and further reproduced in the present disclosure in FIG. 2. In the embodiment shown, the driver 31 forms an element generally corresponding to the driver of the device shown in FIG. 1, i.e. bushing 82. An outer helical track 33 is disposed on the driver 31. A dose setting limiter is defined by nut member 32 which is threadedly coupled to helical track 33 of driver 31. Further, in FIG. 2, a dose setting element 30 corresponds to the scale drum 80 of FIG. 1. At its outer wall the nut member 32 is in the axial direction provided with a recess 34 which is engaged by a ridge 35 in the axial direction on the inner side of the dose setting element 30.

The helical track has a length which correlates with the total amount of drug in a new full cartridge. During dose setting the driver 31 remains non-rotatable while the dose setting element 30 rotates. Hence, when dialing up a dose the nut member 32 moves towards an end stop of helical track 33. During dose expelling the driver 31 rotates with the dose setting element 30. Hence nut member 32 maintains its present position relative to helical track 33. The nut member 32 only abuts the end stop of the helical thread 33 when the sum of accumulated expelled doses and the present set dose equals the total amount of liquid drug in a full cartridge. This prevents setting a dose that exceeds the amount of liquid drug remaining in the cartridge.

The shown end-of-content limiter provides only a non-limiting example of a suitable end-of-content limiter to be used in connection with the injection device shown in FIG. 1. Other known end-of-content limiters may alternatively be used in the injection device, such as the end-of-content limiters disclosed in WO 2006/128794 A2, WO 2010/149209 A1 and WO 2013/156224 A1. In accordance with such end-of content mechanisms, instead of an end-of-content limiter formed as a nut member as such, a corresponding track follower that does not necessarily be formed as a "nut" may be used instead, where the track follower may include a first track coupling being coupled to a driver and a second track coupling being coupled to a dose setting element. When used in the present disclosure, the term "nut member" and "end-of-content limiter" will encompass any type of end-of-content limiter.

In accordance with the assembling procedure of the prior art injection device shown in FIG. 1, the device may be assembled by forming a distal subassembly which includes distal housing component 2, cartridge 89, piston washer 9, nut element 40 and piston rod 7. In distal subassembly, the nut element 40 is secured relative to the distal housing component 2 at a particular predefined axial position by means of an axial snap fit. The piston rod 7 is provided in an already threadedly engaged state relative to nut element 40 where the piston rod 7 assumes a particular rotational orientation relative to distal housing component 2 and where the distal end of the piston rod is in close proximity with the piston washer 9, the piston washer being located adjacent the piston of cartridge 89.

The proximal subassembly includes the remaining components of the injection device, i.e. the proximal subassembly includes the proximal housing component 1 and the dose setting and expelling mechanism in a state where the nut member 32 assumes a pre-defined start position relative to the helical track of the driver (i.e. bushing 82) and where the driver tube 85 assumes a predefined rotational orientation relative to the proximal housing component 1. This allows the piston rod 7 to slide into engagement with the driver tube 85 as the distal subassembly is axially brought into engagement with the proximal subassembly for finally securing the two subassemblies relative to each other, this without requiring relative rotation between piston rod 7 and driver tube 85.

Production tolerances on the piston rod, the dose setting and expelling mechanism, cartridge body, cartridge filling level and other components result in variations in piston rod position and piston position in each device during assembly.

In mechanical devices production, in order to minimize a potential clearance between the piston rod and the piston of the cartridge, positioning may be carried out by initially positioning the piston rod 7 in a nominal position. Due to tolerances various different clearance gaps between the piston and the piston rod will show when the distal and proximal subassemblies of each sample are permanently secured together. On the basis of measurements or estimations, which may be performed at different steps of the assembly process, the actual gap in each sample traditionally has been eliminated or at least partly reduced by operating the dose setting and expelling mechanism. Operating the dose setting and expelling mechanism may be carried out either after final assembly or prior to final assembly of the different subassemblies. However such compensation procedure means that the end-of-content mechanism will be operated to a lesser or higher degree even before the device is shipped to the user meaning that the experienced total doseable volume varies from sample to sample. Generally such variations and inconsistencies from one sample to another should be avoided as this may provide the impression that the quality of the device could be somewhat non-optimal.

Turning now to FIG. 3 and FIGS. 4*a*-4*f* a first embodiment of an improved drug delivery device and assembly method will now be described. In FIG. 3 an improved distal housing component 102 is shown exhibiting a pair of axial indentations 102*c* extending in distal direction from a proximal end face of distal housing component 102. Also shown is an improved nut element 140 which again includes a central opening which is provided with an inner thread 140*a* adapted to cooperate with an external thread 107*a* of piston rod 107. Nut element 140 includes a pair of radially extending protrusions each sized to be received in a respective indentation 102*c* in distal housing component 102. The pairs of indentations 102*c* and protrusions 140*c* enable adjustment of the axial position of the nut element 140 while the engagement between the components is maintained preventing relative rotational movement. The axial indentations 102*c* are so configured that the nut element 140 is variably positionable into a range of different axial positions for fine tuning the axial position of the nut element 140 to eliminate or reduce a potential air gap between a held piston rod 107 and a piston 199 of a held cartridge 189. FIG. 3 further shows a piston washer 109 as well as a held cartridge 189 accommodated within distal housing component 102.

Figure 4A:
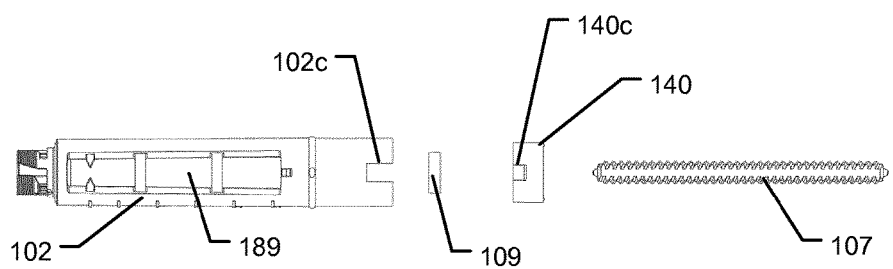

In FIG. 4*a*, a schematic view depicts the components intended to form a distal subassembly 1020 according to the first embodiment. Distal housing component 102 accommodates a drug filled cartridge 189. Piston washer 109 is lined up for being inserted adjacent the piston of the cartridge 189. Also the nut element 140 and the piston rod 107 are shown. The series of pictures are schematic since real life production would be performed at multiple assembly stations in parallel.

Figure 4B:
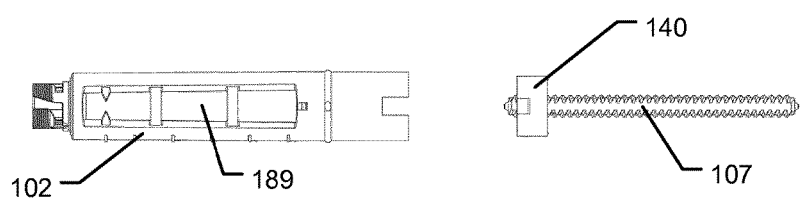

FIG. 4*b* shows a subsequent state after insertion of piston washer 199 in the distal housing component 102 so that the piston washer 109 is in abutting engagement with the piston 199 of the held cartridge 189. Furthermore, the piston rod 107 and the nut element 140 are brought in threaded engagement 107*a*/140*a* with each other to form a piston rod assembly. The piston rod 107 is held in a predefined rotational and axial orientation relative to the nut element 140.

Figure 6:
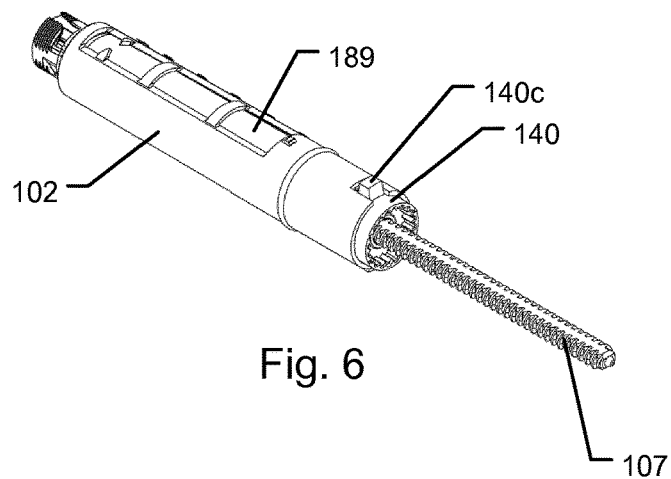
FIG. 6 is a perspective view of components for the distal subassembly in the state shown in FIG. 4c.
Figure 4C:
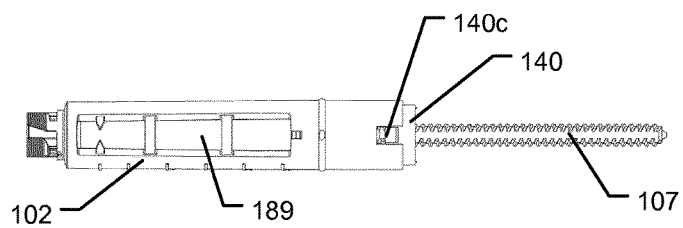

In FIG. 4*c* and FIG. 6 the piston rod assembly has been axially moved into partial engagement with the distal housing component 102 so that the radial protrusions 140*c* are received in the indentations 102*c* preventing relative rotation between nut element 140 and distal housing component 102. The axial position of nut element 140 relative to the distal housing component may be selected to assume a nominal axial position where a minimum clearance between the piston rod 107 and the piston washer is ensured 109. The forming of the distal subassembly is preferably made while holding the proximal end of the distal housing component pointing upwards so that the piston washer 109 abuts the piston of the held cartridge 189.

Figure 7:
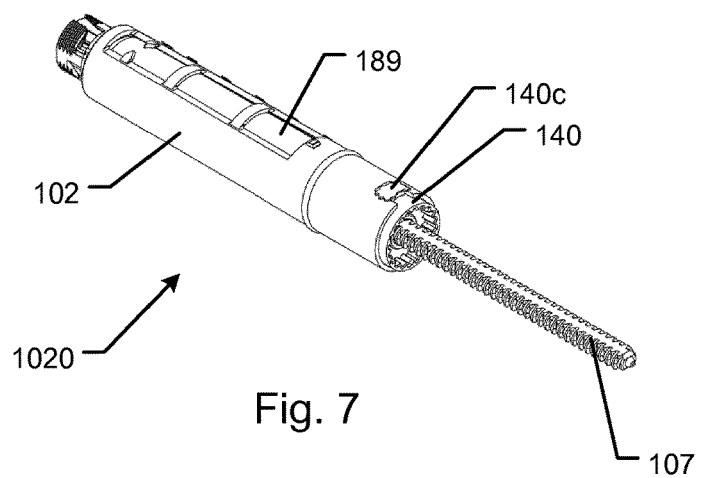
FIG. 7 is a perspective view of a final distal subassembly for a device of first embodiment in the state shown in FIG. 4d.
Figure 4D:
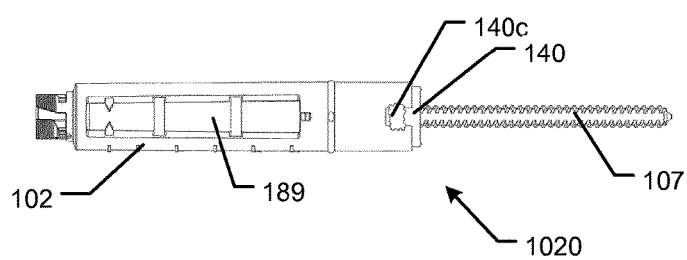

Subsequently, as shown in FIGS. 4*d* and 7, the piston rod assembly 107/140 has been moved axially relative to the distal housing component 102 so that a predetermined axial clearance or abutment between the piston rod 107 and the piston washer 109 is obtained. The movement may be performed under control of any type of measurement providing positioning feedback. Suitable methods may include optical measurements, force measurements or similar methods. If a clearance of predetermined magnitude is aimed at, optical measurements may be used or alternatively a force measurement may be used for ensuring abutment with subsequent predetermined axial movement creating the desired clearance.

The axial movements of piston rod assembly 107/140 with respect to the distal housing component 102 may occur while rotationally maintaining the piston rod 107 in a predetermined rotational orientation relative to the distal housing component 102 in order to ensure problem-free rotational mating between the piston rod 102 and the driver tube 85 during subsequent assembly steps.

As shown in FIGS. 4d and 7, when the piston rod assembly 107/140 assumes the desired axial position relative to the distal housing component 102, the nut element 140 is permanently secured to the distal housing component 102. Permanent attachment may be performed using any suitable fastening method such as by means of an adhesive or joining using laser radiation, ultrasonic welding or induction welding. Still alternative methods may include use of mechanical fastening elements. In the state shown in FIGS. 4d and 7, the distal subassembly 1020 has been finalized.

Figure 4E:
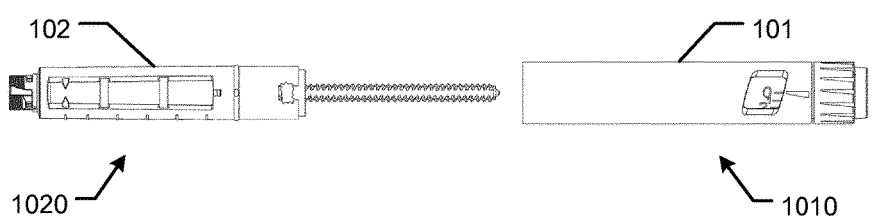

In FIG. 4e a proximal subassembly 1010 comprising the proximal housing component 101 and the remaining parts of the device is axially aligned with the distal subassembly 1020.

Figure 4F:
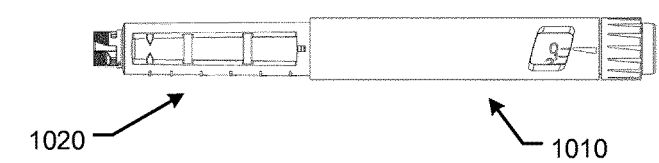
Figure 5:
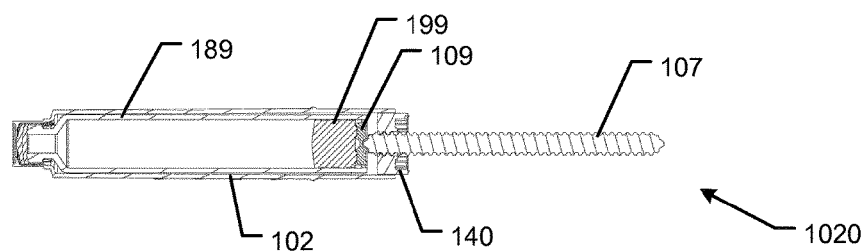

The proximal subassembly 1010 has been formed ensuring a predefined rotational orientation of the driver tube 85 subsequently enabling the driver tube to move axially into engagement with the piston rod 107 to provide the rotational engagement between the driver tube 85 and the piston rod 107 in a way where relative axial movements are allowed. By moving the proximal subassembly and the distal subassembly axially relative to each other the two subassemblies are brought together enabling the snap fit engagement between the distal housing component 102 and the proximal housing component 101 to be established. This state is shown in FIG. 4f. The assembly method has been provided so that the distal housing component 102 and the proximal housing component 101 has a proper rotational orientation relative to each other so that the intended rotational alignment between a window opening for the scale drum with the inspection openings of the cartridge holder is ensured. The assembled injection device is now ready for labelling and other subsequent finalization steps.

The above method may include a procedure which may be phrased a "standard dose setting and expelling procedure" to be performed either before the state shown in FIG. 4e or subsequent to the state shown in FIG. 4f. The "standard dose setting and expelling procedure" may be the same and of same magnitude across the individual devices of the production line. Such dose setting and expelling procedure may for example be carried out for performing a function check for the dose setting and expelling mechanism and/or for elimination of a previously established predefined and fixed "standard gap".

In other embodiments, between distal housing component 102 and nut element 140 a series of micro detents may be arranged to provide relative axial variation to be performed in a series of predefined axial increments. Thus an axial detent mechanism may be provided between the distal housing component 102 and the nut element 140 which enables initial axial adjustment and subsequent final axial fixation.

Figure 8:
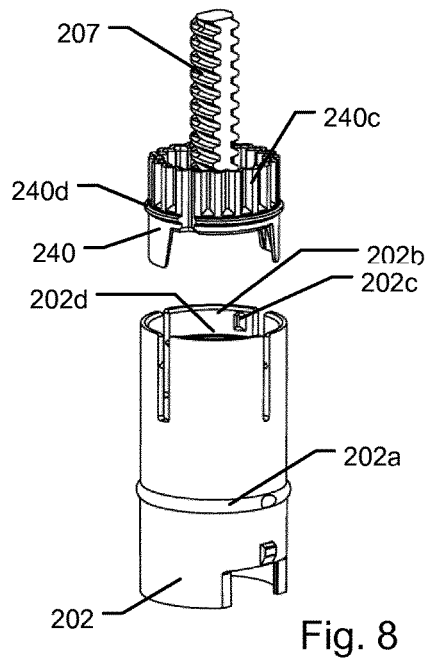
FIG. 8 is an exploded perspective view of details of components of a distal subassembly according to a second embodiment.
Figure 10:
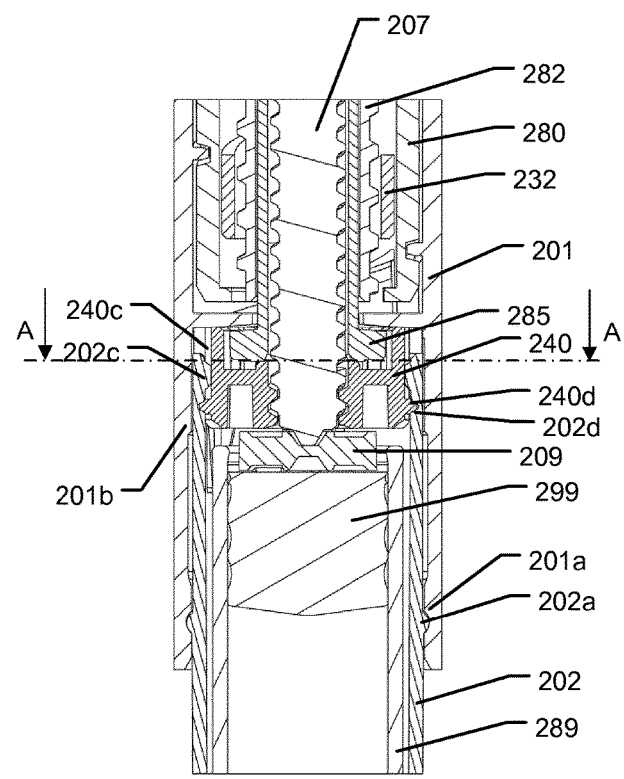
FIG. 10 is a cross sectional detailed view of main components of the assembled device according to the second embodiment.
Figure 9:
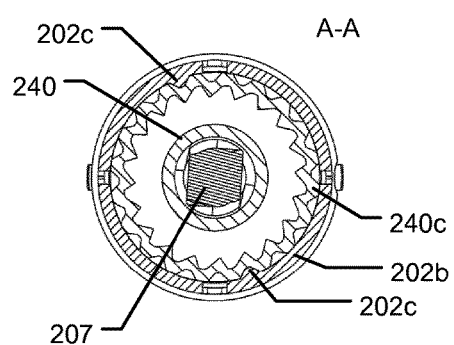
FIG. 9 is a cross sectional axial view in distal direction of selected parts of a distal subassembly according to the second embodiment.

Turning to FIG. 8-10 a second embodiment of an improved drug delivery device and assembly method will be described. In FIG. 8 select components of a distal subassembly according to the second embodiment is shown. In addition to a piston rod 207, an improved distal housing component 202 and an improved nut element 240 are shown. The distal housing component 202 includes a peripheral wall where axially running slits divide the proximal part of the distal housing component into four annular sections 202b. Each annular section 202b is resilient in the radial direction. A plurality of inner protrusions 202c is provided at regular intervals around the circumference, the protrusions extending radially inwards from the annular sections 202b. The improved nut element 240 includes a plurality of teeth 240c adapted to cooperate with the inner protrusions 202c so that a rotational detent mechanism is formed. The nut element 240 includes a circumferential outwards protruding ledge 240d which is configured for being received in a circumferential groove 202d provided at an inner peripheral surface of distal housing component 202. When the nut element 240 is properly axially positioned relative to the distal housing component 202 the ledge 240d snaps into groove 202d allowing relative rotational movement between nut element 240 and distal housing component 202 but preventing axial displacement. When the nut element 240 is inserted in the proper axial position relative to distal housing component 202, and prior to mating with the proximal housing component 201, the detent mechanism 202c/240c enables rotation of nut element 240 relative to distal housing component 202 to be performed in incremental steps, in this embodiment in incremental angular steps of 18 deg.

For the assembly method according to the second embodiment, the distal subassembly is formed by firstly inserting the cartridge 189 in the distal housing component 202, then assembling the piston rod 207 with the nut element 240 to establish the threaded engagement there between, and finally inserting the nut element 240 into a proper axial position relative to distal housing component 202. Prior to this a piston washer 209 has been positioned adjacent the piston 299 of a held cartridge 289. In this initial state the distal subassembly has been formed, and the piston rod 107 is held in a predefined rotational orientation relative to the distal housing component 202.

Next, the axial position of piston rod 207 and piston washer 209 may be varied by performing relative rotation between the nut element 240 and the distal housing component 202 by means of the detent mechanism 202c/240c. This occurs while the piston rod 107 is held in a predefined rotational orientation relative to the distal housing component 202. The rotation between nut element 240 and distal housing component 202 is performed until a predetermined axial clearance or abutment between the piston rod 207 and the piston washer 209 is obtained.

Just like the first embodiment, the proximal subassembly is assembled comprising the proximal housing component and the remaining parts of the device. Again the proximal housing component accommodates an end of content limiter mechanism provided by bushing 282, end of content limiter 232 and dose setting element 280. The proximal subassembly is axially aligned with the distal subassembly. The proximal subassembly has been formed ensuring a predefined rotational orientation of the driver tube 285 so that the driver tube easily rotationally align and engages the piston rod 207 allowing axial displacement there between. By moving the proximal subassembly and the distal subassembly axially relative to each other the two subassemblies are brought together enabling the snap fit engagement between the distal housing component 202 and the proximal housing component 201 to be established. This state is shown in FIG. 10.

A distal peripheral portion of the proximal housing component 201 is formed to cooperate with distal housing component 202 upon assembling acting to compress the annular sections 202b of distal housing component 202 radially inwards into fixed engagement with the teethed surface 240d thereby immobilizing the rotational detent mechanism. Hence, when the snap connection between distal housing component 202 and the proximal housing component 201 is established the nut element 240 is prevented from rotating relative to the distal housing component 202.

The assembly method has been arranged so that the distal housing component 202 and the proximal housing component 201 has a proper rotational orientation relative to each other so that the intended rotational alignment between a window opening for the scale drum with the inspection openings of the cartridge holder is ensured. The assembled injection device is now ready for labelling and other subsequent finalization steps.

As an alternative to the rotational locking mechanism described for locking the nut element 240 in a particular rotational position relative to the distal housing component 202, alternative locking means may be used either alone or in combination with the described locking mechanism. Alternative locking means may include using an adhesive or by joining the nut element 240 relative to the distal housing component 202 and/or to the proximal housing component 201 by using ultrasonic welding, laser radiation or like processes.

By using the described design of embodiment 1 and 2 and their respective assembly methods, the clearance of each individual pen device can be effectively eliminated or alternatively reduced to a level which is uniform between individual pen devices. In situations where and end-of-content mechanism is incorporated into the device, the pen manufacturing and assembly can be carried out without use of the dose setting and expelling mechanism for evening out the gap between the piston rod and the piston and thus further enables the end-of-content mechanism of each individual device to provide a consistent, pre-defined, and uniform total doseable quantity from each individual pen device.

In a further not shown embodiment which resembles the embodiment shown in FIGS. 3-7, instead of forming the distal housing component 102 and nut element 140 with geometries ensuring axial variability between the two components by a non-rotational relative axial movement, an alternative coupling between the distal housing component 102 and the nut element 140 may be provided by means of a threaded engagement. By designing the lead of this threaded engagement differing in an appropriate manner from the lead of the threaded engagement 107*a*/140*a*, the rotation of the nut element 140 relative to the distal housing component 102 will effectively move the piston rod 107 relative to the piston 199 of the cartridge 189. Hence, by rotating the nut element 140 relative to the distal housing component 102, optionally while keeping the piston rod 107 rotationally fixed relative to the distal housing component 102, the clearance between the piston rod and the piston may be adjusted to assume a predefined gap or, alternatively, to eliminate the clearance entirely. The said threaded engagement between the nut element 140 and the distal housing component 102 may be supplemented by a rotational detent mechanism so that the rotation of the nut element 140 relative to the housing component 102 may be performed in pre-defined angular steps. One non-limiting example of such rotational detent mechanism may be provided in a way which resembles the rotational detent mechanism 202*c*/240*c* shown in FIG. 8.

The injection device shown in FIG. 1 provides a non-limiting example of a manual pen injector where the expelling mechanism is fully manual in which case the dose setting element and the injection button moves proximally during dose setting corresponding to the set dose size, and then is moved distally by the user to expel the set dose, this corresponding to the shown embodiments.

In alternative embodiments of injection devices these may incorporate an energy storage aiding to expel a set dose when a user operates a dose injection button. Depending on the type of expelling mechanism embodied in a given drug delivery device, the expelling mechanism may comprise a spring which is strained during dose setting and then released to drive the piston rod when the release button is actuated. Still other alternative mechanisms may include a spring member which stores sufficient energy for expelling the total contents of a cartridge during one or more separate dose administrations. Each such type of injection devices can be structured to enable assembly by the above described methods and features in accordance with the different aspects of the present invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method of assembling a drug delivery device defining a distal drug outlet end and an opposite proximal end, wherein the drug delivery device in the assembled state defines a distal housing component secured to a proximal housing component, wherein:
   the distal housing component structured to hold a cartridge comprising a liquid drug and a piston slideably arranged therein in an axial direction, a nut element having a threaded opening and a piston rod comprising an outer thread engaged with the threaded opening of the nut element, and
   the proximal housing component houses a dose setting and expelling mechanism comprising a driver adapted to rotationally couple to the piston rod so as to prevent relative rotational movement but allow relative axial slideable engagement between the driver and the piston rod, the driver being rotatable during a dose expelling procedure to induce rotation on the piston rod to rotate the piston rod through the nut element and causing a dose of drug to be expelled, and
   wherein the method of assembling comprises the steps of:
      a1) providing the distal housing component and the nut element so configured that, in an initial state, the nut element and the distal housing component are positionable relative to each other in a series of predetermined variable positions for varying the axial position of the piston rod relative to the piston of the cartridge, when present, and wherein the nut element is selectively fixable relative to the distal housing component in each of said predetermined variable positions,
      a2) providing and arranging the cartridge in the distal housing component,
      a3) arranging the piston rod and the nut element in threaded engagement with each other to form a piston rod assembly and arranging the piston rod assembly relative to the distal housing component so that the piston rod is arranged with an initial axial clearance relative to the piston of the cartridge, when present,
      a4) rearranging the nut element and the distal housing component relative to each other in one of a series of predetermined relative orientations to reduce said initial axial clearance while rotationally maintaining the piston rod in a predetermined rotational orientation relative to the distal housing component to obtain a predetermined axial clearance or abutment between the piston rod and the piston, a5) securing the nut element relative to the distal housing component into one of said series of predetermined relative orientations for maintaining said predetermined axial clearance or abutment between the piston rod and the piston, b1) providing the proximal housing component with the drive mechanism wherein the driver assumes a predetermined rotational orientation relative to the proximal housing component, c1) arranging the distal housing component and the proximal housing component relative to each other in a predetermined rotational orientation, c2) moving the distal housing component and the proximal housing component axially relative to each other so that the driver engages in axially slideable engagement with the piston rod, and c3) fixedly securing the distal housing component and the proximal housing component relative to each other in a predetermined relative axial position.

2. The method according to claim 1, wherein in step c2), the piston rod is held rotationally stationary relative to the distal housing component and wherein the driver is held rotationally stationary relative to the proximal housing component.

3. The method according to any of claim 1, wherein in step a3) of arranging the piston rod assembly relative to the distal housing component the nut element is brought into engagement with the distal housing component.

4. The method according to any of claim 1, wherein in the course of step a4) engagement between the nut element and the distal housing component is maintained.

5. The method according to any of claim 1, wherein the nut element and the distal housing component are configured for, in an initial state, being engaged with each other in a predetermined relative axial position while allowing relative rotational position variation and wherein, the step a4) of rearranging the nut element relative to the distal housing component in one of a series of predetermined relative orientations is performed by varying the relative rotational position between the nut element and the distal housing component through a series of predetermined relative rotational positions.

6. The method according to claim 5, wherein a rotational detent mechanism is provided between the nut element and the distal housing component enabling, during step a4), the relative rotational position between the nut element and the distal housing component to be selectably retained in a selective one of a series of discrete rotational positions.

7. The method according to claim 6, wherein the proximal housing component is configured for cooperating with at least one of the distal housing component and the nut element for preventing relative rotation away from a selected discrete rotational position and wherein in step a5) of securing the nut element relative to the distal housing component is established during step c2) in the course of moving the distal housing component and the proximal housing component axially relative to each other.

8. The method according to any of claim 1, wherein the nut element and the distal housing component are configured for, in an initial state, being engaged with each other in a predetermined relative rotational orientation while allowing relative axial position variation and wherein, in step a4) of rearranging the nut element relative to the distal housing component into one of a series of predetermined relative orientations is performed by varying the relative axial position between the nut element and the distal housing component through a series of predetermined relative axial positions.

9. The method according to any of claim 1, wherein the outer thread of the piston rod and the threaded opening of the nut element defines a first threaded engagement having a first lead, wherein the nut element is coupled with the distal housing component via a second threaded engagement of second lead being different than the first lead of the first threaded engagement, and wherein in step a4) of rearranging the nut element relative to the distal housing component in one of a series of predetermined relative variable orientations is performed by operating the nut element through the second threaded engagement with the distal housing component thereby varying the relative axial position between the nut element and the distal housing component.

10. The method according to any of the claim 1, wherein the dose setting and expelling mechanism comprises a dose setting element that rotates relative to the driver during setting of a dose and wherein the dose setting element and the driver rotates together during expelling of a set dose, and wherein an end-of-content limiter is arranged between the driver and the dose setting element, the end-of-content limiter being configured to prevent setting of a dose which exceeds a doseable amount of liquid drug remaining in the cartridge, when present.

11. The method according to claim 10, wherein the end-of-content limiter is engaging the driver and the dose setting element and wherein the end-of-content limiter moves towards an end-of-content stop geometry provided by one of the driver and the dose setting element as the dose setting element is rotated relative to the driver for dialing up a dose.

12. The method according to any of the claim 10, wherein in step a4), obtaining a predetermined axial clearance between the piston rod and the piston and wherein subsequent to step c2) of providing axially slideable engagement between the driver and the piston rod, the dose setting element is operated for rotating the driver in a predetermined angular movement to cause the piston rod to abut the piston of the cartridge, when present.

13. The method according to any of the claim 1, wherein the drug delivery device in the assembled state comprises a piston washer arranged between the piston and the piston rod and adapted to transfer an axial force from the piston rod to the piston and wherein the method comprises the steps, in step a2), of providing the piston washer and positioning the piston washer adjacent the piston.

14. A drug delivery device assembled in accordance with the method as defined in claim 1.

15. A drug delivery device defining a distal drug outlet end and an opposite proximal end, the drug delivery device comprising a distal subassembly and a proximal subassembly attached to the distal subassembly, wherein:

the distal subassembly comprises a distal housing component structured to hold a cartridge comprising a liquid drug and a piston slideably arranged therein in an axial direction, a nut element having a threaded opening and a piston rod comprising an outer thread engaged with the threaded opening of the nut element, and the proximal subassembly comprises a proximal housing component that houses a dose setting and expelling mechanism comprising a driver adapted to rotationally couple to the piston rod of the distal subassembly so as to prevent relative rotational movement but allow relative axial slideable engagement between the driver and the piston rod, the driver being configured for being rotated during a dose expelling procedure to induce rotation on the piston rod to rotate the piston rod through the nut element and causing a dose of drug to be expelled, and wherein the distal housing component and the nut element are so configured that before attaching the distal subassembly to the proximal subassembly, the nut element and the distal housing component are positionable relative to each other in a series of predetermined variable positions for varying the axial position of the piston rod relative to the piston of the cartridge, when present, and wherein the nut element is selectively fixable relative to the distal housing component in each of said predetermined variable positions.

* * * * *